(12) United States Patent
Bucher et al.

(10) Patent No.: US 8,536,208 B2
(45) Date of Patent: Sep. 17, 2013

(54) ANTIFUNGAL COMPOSITION

(75) Inventors: Christian Bucher, Basel (CH); Günter Ditzinger, Freiburg (DE); Estelle Dubois, Lyons (FR); Delphine Marchaud, Saint Andéol le Chateau (FR)

(73) Assignee: Basilea Pharmaceutica AG, Basel (CH)

( * ) Notice: Subject to any disclaimer, the term of this patent is extended or adjusted under 35 U.S.C. 154(b) by 488 days.

(21) Appl. No.: 12/674,048

(22) PCT Filed: Aug. 20, 2008

(86) PCT No.: PCT/EP2008/060905
§ 371 (c)(1),
(2), (4) Date: Nov. 24, 2010

(87) PCT Pub. No.: WO2009/024590
PCT Pub. Date: Feb. 26, 2009

(65) Prior Publication Data
US 2011/0281918 A1    Nov. 17, 2011

(30) Foreign Application Priority Data
Aug. 21, 2007  (EP) .................................. 07114652

(51) Int. Cl.
*A01N 43/78* (2006.01)
*A01N 55/02* (2006.01)
*A01N 43/64* (2006.01)
*A61K 31/41* (2006.01)
*A61K 31/555* (2006.01)

(52) U.S. Cl.
USPC ............................ 514/365; 514/184; 514/383

(58) Field of Classification Search
USPC .......................... 514/365, 184, 383
See application file for complete search history.

(56) References Cited

U.S. PATENT DOCUMENTS

| 6,054,136 | A | 4/2000 | Farah |
| 6,652,865 | B2 | 11/2003 | Benameur |
| 2004/0146538 | A1* | 7/2004 | Benameur et al. ............. 424/400 |
| 2005/0186142 | A1 | 8/2005 | Tamarkin |
| 2009/0149434 | A1* | 6/2009 | Podolski ....................... 514/179 |

FOREIGN PATENT DOCUMENTS

| EP | 0667346 | 8/1995 |
| EP | 1280795 | 3/2005 |
| WO | 9945008 | 9/1999 |

OTHER PUBLICATIONS

Hong et al., "A new self-emulsifying formulation of itraconazole with improved dissolution and oral absorption," Journal of Controlled Release, vol. 110, No. 2, Jan. 10, 2006, pp. 332-338.
The International Search Report and Written Opinion by the International Searching Authority, issued on Apr. 22, 2009, in the PCT application No. PCT/EP2008/060905.

* cited by examiner

*Primary Examiner* — Sreeni Padmanabhan
*Assistant Examiner* — Uma Ramachandran

(57) ABSTRACT

A pharmaceutical composition for oral administration which is self-emulsifying on contact with an aqueous phase, in particular gastrointestinal fluids, and which comprises: (a) an antifungally active compound of formula (I) wherein $R^1$, $R^2$ and $R^3$ are independently of one another hydrogen, F or Cl; or a pharmaceutically acceptable acid addition salt thereof, and (b) a carrier comprising a solubilizer component for the antifungally effective component (a).

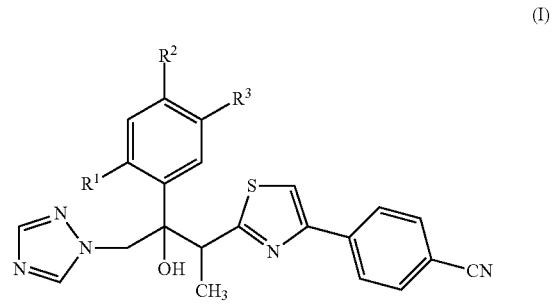

(I)

33 Claims, No Drawings

ANTIFUNGAL COMPOSITION

This application is a National Stage Application of PCT/EP2008/060905, filed Aug. 20, 2008, which claims priority from European Patent Application 07114652.6 filed on Aug. 21, 2007. The priority of both said PCT and European Patent Application is claimed.

The invention relates to improved pharmaceutical compositions for oral use comprising antifungal drugs, in particular antifungally active compounds of formula (I):

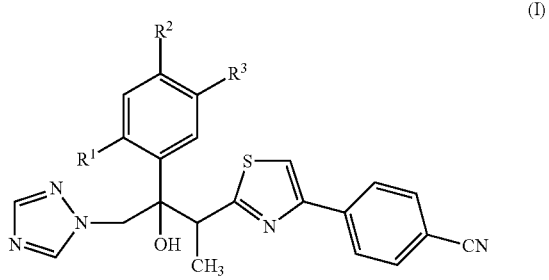

(I)

wherein
$R^1$, $R^2$ and $R^3$ are independently of one another hydrogen, F or Cl; or pharmaceutically acceptable acid addition salts thereof, like for instance 3-[4-(4-cyanophenyl)thiazol-2-yl)]-2-(2,5-difluorophenyl)-1-(1H-1,2,4-triazol-1-yl)-butan-2-ol described in WO-A-99/45008 (also known as BAL 4815), or ravuconazole, 3-[4-(4-cyanophenyl)thiazol-2-yl)]-2-(2,4-difluorophenyl)-1-(1H-1,2,4-triazol-1-yl)-butan-2-ol, i.e. the 2,4-difluorophenyl analogue of the aforementioned compound and described in EP-A 0 667 346, or their acid addition salts. Compositions comprising antifungals like these are vital, in particular for the oral treatment of serious systemic mycoses like for instance disseminated aspergillosis.

The compounds of formula (I), however, like many other pharmaceutical drugs, are rather lipophilic and accordantly of very poor solubility in aqueous media. This applies also to many salts of said drugs, e.g. the hydrochloric acid addition salts. As a consequence of the limited solubility of said drugs in aqueous media, their bioavailability is also rather low normally after oral administration, so that it is difficult to retain a therapeutically effective concentration.

One very popular approach known in the art for overcoming the bioavailability problems with strongly lipophilic compounds is the design of suitable prodrugs exhibiting an improved solubility in water, a strategy which has also been tried e.g. in case of 3-[4-(4-cyanophenyl)thiazol-2-yl)]-2-(2,5-difluorophenyl)-1-(1H-1,2,4-triazol-1-yl)-butan-2-ol (BAL 4815) disclosed e.g. in EP-A-1 280 795 directed to certain prodrugs of said antifungally active compound. A similar approach was tried followed with the corresponding 2,4-difluorophenyl derivative (ravuconazole) which has been converted into its di-lysine phosphoester (BMS-379224) in order to improve its solubility in aqueous media.

Other well known means for improving the bioavailability of poor water soluble compounds, are either the formation of particles of the drug substance in the sub-micron range (micro- or nanoparticles), or the formation of solid solutions or solid dispersions, each appropriately incorporated into orally applied formulations (like tablets or capsules). These technologies improve the intrinsic dissolution of these compounds, and thus by increasing the concentration gradient at the epithelial cell barrier in the gastro-intestinal (GI) tract, enhancing the oral bioavailability.

A further, more recent approach for improving the bioavailability of poorly soluble drugs after oral administration is the formulation of said drugs in so called Self-Emulsifying Drug Delivery Systems (SEDDS) or Self-Microemulsifying Drug Delivery Systems (SMEDDS), compositions of matter comprising a lipid phase for dissolving the lipophilic drug and one or more suitable surfactant(s)/co-surfactants. Because of a thoroughly selected combination of incorporated surfactant(s) and co-surfactant(s) these systems tend to instantly form micelles when coming into contact with aqueous media, in particular gastrointestinal fluids, thus leading to pseudo-solubilization and enhanced absorption of the drug in the gastro-intestinal (GI) tract.

U.S. Pat. No. 6,054,136 discloses such systems as a means for increasing the bioavailability of drugs, which are difficult to dissolve. Exemplified are systems for delivery of oral indomethacin and diclofenac sodium, i.e. of compounds being strongly different in chemical structure from the compounds of formula (I). Said self-emulsifying drug delivery systems are based on a mixture of unsaturated $C_8$-$C_{18}$ polyglycolized glycerides with a HLB (Hydrophilic-Lipophilic-Balance) value equal to 6 (LABRAFIL® WL 2609 BS) as the lipophilic phase, $C_8$-$C_{10}$ polyglycolized glycerides having a HLB value of less than 16 (LABRASOL®) as the surfactant and a polyglycerol oleate of HLB value 10 (PLUROL OLEIQUE®) as the co-surfactant of the drug delivery system.

Another prior art reference, U.S. Pat. No. 6,652,865, discloses self-microemulsifying systems which are intended to improve the systemic bioavailability of statin derivatives, which are subject to relatively high intestinal first-pass metabolism, in particular simvastatin, by inhibition of this first pass metabolism. The self-microemulsifying system used is a mixture of a lipophilic phase comprising a mixture of glycerol mono-, di- and/or triesters and polyethylene glycol mono- and/or diesters with at least one fatty acid selected from the group comprising $C_8$-$C_{18}$-fatty acids having an HLB value of less than 20, including the commercial products GELUCIRE® 44/14 (a lauroyl macrogolglyceride) and LABRAFIL® M1944CS (an oleoyl macrogolglyceride)

a surfactant phase comprising a mixture of glycerol mono-, di- and/or triesters and polyethylene glycol mono- and/or diesters with caprylic acid and capric acid having an HLB value between 5 and 20, including the commercial product LABRASOL® (a caprylocaproyl macrogolglyceride); and a co-surfactant phase comprising at least one ester of an alcohol with at least one fatty acid chosen from the group comprising caprylic esters of propylene glycol, lauric esters of propylene glycol and oleic esters of polyglycerol, including the commercial products CAPRYLOL® 90 (propylene glycol monocaprylate), CAPRYOL®PGMC (a propyleneglycol caprylate) and LAUROGLYCOL® 90 (propyleneglycol monolaurate).

Beside the above mentioned constituents, numerous other excipients for formulating pharmaceutically useful self-(micro)emulsifying drug delivery systems have been found or newly developed during the last years, many of which are also commercially available, e.g. from Gattefossé S.A., F-Saint-Priest.

In "A new self-emulsifying formulation of itraconazole with improved dissolution and oral absorption"; J. Control: Release (2006) 110(2), 332-338, Hong J Y et al. suggest such a self-emulsifying drug delivery system for improving the bioavailability of a sparely soluble antifungal drug, too, namely of itraconazole, in order to render the compound (more) suitable for oral administration. Itraconazole has the following chemical structure:

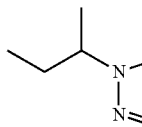
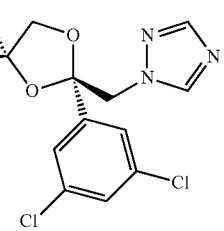

According to the reference, it was found that a mixture of (ethoxyethoxy)ethanol (Transcutol); the non-ionic polyoxyethylene-polyoxypropylene co-polymer available under the tradename Pluronic® L64 (CAS-No. 11104-97-5) and tocopherol acetate provided the maximum solubility for itraconazole, and that this solubility was still further improved when HCL was added. It was further shown that this mixture greatly enhanced the bioavailability of itraconazole after oral dosage, and independently from an eventual food intake.

Whereas the principle of self-(micro)emulsifying drug delivery systems thus appears—at a first glance—to be readily applicable for rendering poorly water-soluble drugs, including the antifungal drug itraconazole, more bioavailable after oral administration, only very few pharmaceutical products on the market have successfully been formulated as a self-(micro)emulsifying system, although the number of hydrophobic drugs has significantly increased in recent years. However, not every hydrophobic drug qualifies for such systems and, on the other hand, slight differences in chemical structure of a drug frequently require the use of a differently composed system, so that the design of an appropriate self-emulsifying drug delivery system is actually limited to the use of compounds of a rather specific chemical structure only. On the other side, the known efficacy of a certain system for a specific type of drug does not allow to prognosticate, how said system would work with another drug, and/or how the known system can systematically be changed to make it work with another drug. Simple routine adjustment of an existing self-(micro) emulsifying drug delivery system is at most promising for a chemically very closely related drug, if at all, but it remains a difficult problem to design such a system for any new type of drug which appears sufficiently efficient for practical use.

In particular, in case of the antifungal drugs of formula (I) (BAL 4815 or ravuconazole, respectively), the prodrug approach for improving their water solubility was obviously preferred by those skilled in the art.

It has now surprisingly been found that the compounds of formula (I) must not necessarily be converted into a prodrug in order to raise their solubility in aqueous media and/or their oral bioavailability as done so far in the art, but that these compounds can be effectively be formulated as a self-emulsifying or self-microemulsifying (referred to in the following as "self-(micro)emulsifying") drug delivery system. Accordingly, the present invention provides a self-(micro)emulsifying drug delivery system for improving the solubility of compounds of the above-indicated formula (I) or of acid addition salts thereof in aqueous media, in particular under the conditions found in the gastrointestinal tract, and for improving the bioavailability of said compounds after oral administration in this way.

A first subject of the present invention is therefore a pharmaceutical composition for oral administration which is self-(micro)emulsifying on contact with an aqueous phase, in particular gastrointestinal fluids, and which comprises:
(a) an antifungally active compound of formula (I):

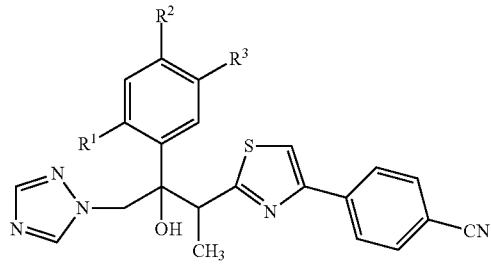

wherein
$R^1$, $R^2$ and $R^3$ are independently of one another hydrogen, F or Cl; or
a pharmaceutically acceptable acid addition salt thereof.

The pharmaceutical compositions for oral administration which is self-(micro)emulsifying on contact with an aqueous phase, in particular gastrointestinal fluids, in accordance with the present invention are meant to be self-emulsifying or self-(micro)emulsifying drug delivery systems (SEDDS/SMEDDS) as mentioned above, i.e. they are substantially isotropic mixtures comprising natural or synthetic oils, solid or liquid surfactants and/or co-surfactants as the essential components. Upon mild agitation followed by dilution in aqueous media, such as GI fluids, these systems can form fine oil-in-water (o/w) emulsions or microemulsions. Self-emulsifying formulations spread readily in the GI tract, and the digestive motility of the stomach and the intestine provide the agitation necessary for self-emulsification. SEDDS typically produce emulsions with a droplet size between 100 and 300 nm while SMEDDS form transparent microemulsions with a droplet size of less than 50 nm. When compared with emulsions, which are sensitive and metastable dispersed forms, self-(micro)emulsifying drug delivery systems are physically stable formulations that are easy to manufacture. For the compounds of formula (I) which exhibits substantially dissolution rate-limited absorption, these systems provide an improvement in the rate and extent of absorption and result in more reproducible blood-time profiles.

The compound of formula (I) is preferably present in the compositions according to the present invention in an amount of 2 to 20, preferably 5 to 15, most preferably 5 to 12 percent by weight, based on the total composition.

More preferably, the present invention concerns a pharmaceutical composition for oral administration which is self- (micro)emulsifying on contact with an aqueous phase, in particular gastrointestinal fluids, and which comprises (a) an antifungally active compound of formula (I) as described before or a pharmaceutically acceptable salt thereof, and
(b) a carrier having an HLB value of less than about 20, preferably less than 16, and comprising a solubilizer component for the antifungally effective component (a) comprising:
  (b1) a mixture of glycerol mono-, di- and/or triesters and of polyethylene glycol mono- and/or diesters with at least one fatty acid chosen from the group comprising $C_8$-$C_{18}$-fatty acids (e.g. Gelucire 44/14; Labrafil M 1944 CS); and/or
  (b2) a mixture of glycerol mono-, di- and/or triesters and of polyethylene glycol mono- and/or diesters with caprylic acid and capric acid (e.g. Labrasol), wherein the antifungally active compound of formula (I) or the pharmaceutically acceptable acid addition salt thereof is present in an amount of 2 to 20 percent by weight based on the total composition, and one of component (b1) or (b2) is present in an amount of 50 or more than 50 percent by weight based on the total composition.

These systems comprise an antifungally effective amount of a compound of formula (I), preferably an amount as already specified above.

For the purposes of the present invention compounds of formula (I) are preferred, wherein
$R^1$ is F or Cl; and
$R^2$ and $R^3$ are independently of one another hydrogen, F or Cl.

Particularly preferred examples of such compounds include the compound of formula (I), wherein $R^1$ and $R^2$ are F; and $R^3$ is hydrogen and its acid addition salts, in particular the hydrochloric acid addition salt, as well as especially the compound of formula (I), wherein $R^1$ and $R^3$ are F; and $R^2$ is hydrogen and its acid addition salts, in particular the hydrochloric acid addition salt which latter substance is the most preferred.

As known from prior art, e.g. U.S. Pat. No. 6,054,136, the formation of the (micro)emulsion on contact of the self-(micro)emulsifying drug delivery system enables normally water-insoluble pharmaceutical drugs to be dissolved instantaneously by presenting them in the form of a multiparticulate supramolecular structure.

The self-(micro)emulsifying drug delivery system according to the present invention for the compounds of formula (I) may be, at ambient temperature (i.e. 10 to 30° C.), in solid or liquid form depending on the nature of the fatty substances of which they are composed.

Consequently and as known, the self-(micro)emulsifying drug delivery system may be incorporated e.g. into hard or soft capsules made from gelatin or from vegetable sources like e.g. hypromellose, in liquid form, optionally while hot, and then, depending on the nature of their constituents, remain liquid or become semi-solid at ambient temperature. The manufacturing process thus usually consists in simply mixing together all the constituents, including the compound of formula (I), with or without heating depending on the physicochemical characteristics of the excipients, and subsequent filling of the mixture into hard or soft capsules, by using standard manufacturing processes, e.g. rotary-dye technology.

In the description hereinbelow and in the claims the expression "aqueous phase" denotes either the in vivo physiological medium as it presents itself after ingesting the composition, the pH of which varies as a function of the state of the gastrointestinal tract, or a reconstituted in vitro physiological medium, the microemulsion then being formed on simple contact with the aqueous phase, without ingestion. All the percentages in this application text are given on a weight basis, if nothing else is stated (percent by weight; % bw).

Component (b1) or component (b2) can e.g. be the main component of the compositions according to the invention being present in an amount of 50 or more than 50 percent by weight of the composition.

In a first embodiment the carrier of the compositions of the present invention comprises (b1) a mixture of glycerol mono-, di- and triesters and of polyethylene glycol (PEG) mono- and diesters with at least one fatty acid selected from the group comprising saturated and unsaturated $C_8$-$C_{18}$ fatty acids as the main component.

In practice, this mixture is e.g. obtained as described in U.S. Pat. No. 6,054,136, by an alcoholysis reaction of a polyethylene glycol having a molecular weight of between 300 and 1500 and of a hydrogenated plant oil itself consisting of a mixture in variable proportions, depending on its nature, of mono-, di- and triglycerides of at least one fatty acid, e.g. caprylic, capric, lauric, myristic, palmitic and/or stearic acid. The mixture may also be obtained e.g. by esterifying glycerol and polyethylene glycol of a molecular weight of between 300 and 1500 with at least one of the fatty acids described above, or alternatively by mixing esters of glycerol and ethylene oxide condensates with at least one of the said fatty acids.

A product corresponding to said definition is e.g. Gelucire®44/14 (sold by Gattefossé S.A., F-Saint-Priest) having an HLB of about 14.

Component (b1) has generally a HLB value of less than 20, preferably less than 16, more preferably from 3 to 15. If component (b1) is the main component of the compositions it is preferably present in amounts of 60 percent by weight and more, most preferably in amounts of 70 to 95 percent of the composition.

In a second embodiment component (b2), i.e. a mixture of glycerol mono-, di- and/or triesters and of polyethylene glycol mono- and/or diesters with caprylic acid and capric acid (e.g. Labrasol), is the main component of the carrier of the compositions according to the present invention.

Such mixtures may be obtained in the same manner as previously described, e.g. by alcoholysis reaction starting with polyethylene glycol with a molecular weight of between 200 and 600 and a hydrogenated plant oil fraction which is rich in glycerol ester, with caprylic acid and capric acid; or by esterifying glycerol and polyethylene glycol with capric acid and caprylic acid, or by mixing an ester of glycerol and ethylene oxide condensates with caprylic acid and capric acid. Preferably, the resulting product has a HLB value of between 5 and 20, more preferably 10 to 20, e.g. about 14.

A product corresponding to the aforementioned definition is e.g. the product Labrasol® (sold by Gattefossé S.A., F-Saint-Priest), a caprylocaproyl macrogol glyceride with a HLB value of about 14, also known to have the function of a surfactant. It corresponds to the monograph of the 4th edition of the European Pharmacopoeia entitled "caprylocaproyl macrogolglyceride". If component (b2) is the main component of the compositions it is preferably present in an amount of 55 to 75 percent, more preferably 55 to 65 percent, by weight of the composition.

The carrier of compositions of the present invention may comprise either component (b1) or component (b2) alone, in particular component (b1) alone, or may as well comprise a mixture of both components (b1) and (b2).

Particularly preferred compositions according to the invention are those which comprise an antifungally active compound of formula (I) in form of the free base.

Particularly, in this type of compositions component (b1) is more preferably present in an amount of 50 or more than 50 percent by weight based on the total composition; and—simultaneously—in an amount of 70 or more than 70 percent by weight of the total carrier.

Other specific embodiments of the present invention comprise a pharmaceutically acceptable acid addition salt of a compound of formula (I), in particular a corresponding hydrochloric acid addition salt.

In one embodiment of this type of composition component (b1) is preferably present in an amount of 50 or more than 50 percent by weight based on the total composition.

In another more preferred embodiment of this type of composition component (b2) is preferably present in an amount of 50 or more than 50 percent by weight based on the total composition; and—simultaneously in an amount of 65 or more than 65 percent by weight of the total carrier.

In a specific embodiment of the latter composition component (b1) comprises a mixture of glycerol mono-, di- and triesters and of polyethylene glycol mono- and diesters with saturated and unsaturated $C_{16}$-$C_{18}$ fatty acids. Products corresponding to this definition are e.g. the products Labrafil®M1944CS and Labrafil®M2125CS (sold by Gattefossé S.A., F-Saint-Priest) and in accordance with the monographs of the 4th edition of the European Pharmacopoeia under the respective names "Oleoyl Macrogolglycerides" and "Linoleoyl Macrogolglycerides".

A more particularly preferred composition according to this type comprises a mixture of glycerol mono-, di- and triesters and of polyethylene glycol mono- and diesters with saturated and unsaturated $C_{16}$-$C_{18}$ fatty acids which has a HLB value of about 4 like Labrafil®M1944CS and represents 15 to 20 percent by weight of the composition.

The carrier of the compositions of the present invention may furthermore comprise further auxiliary components, e.g. a surfactant and/or cosurfactant component ("(co)surfactant"). Suitable (co)surfactants include e.g. particularly nonionic surfactants like sorbitan mono fatty acid esters like e.g. sorbitan monolaurate, sorbitan monopalmitate, sorbitan monostearate or sorbitan monooleate, etc. or polyoxyethylene sorbitan mono fatty acid esters, like e.g. polyoxyethylene sorbitan monolaurates, polyoxyethylene sorbitan monopalmitates, polyoxyethylene sorbitan monostearates or polyoxyethylene sorbitan monooleates, or polyoxyethylene (hydrogenated) castor oil derivatives like e.g. polyoxyethylene 35 castor oil, polyoxyethylene 40 hydrogenated castor oil, or sucrose fatty acid esters, or (poly)glyceryl fatty acid esters like e.g. glyceryl monolinoleate, glyceryl monooleate (e.g. Peceol) or polyglyceryl oleate, and the like. Alternatively, vitamin E tocopherol propylene glycol succinate (Vitamin E TGPS), polyoxyethylene 15 hydroxystearate or decaglycerin monolaurate can be used.

More preferably, however, the carrier of the compositions of the present invention furthermore comprises as an auxiliary component (b3) a component comprising at least one ester of an alcohol with at least one fatty acid selected from the group comprising caprylic esters of propylene glycol, lauric esters of propylene glycol and oleic esters of polyglycerol (e.g. Lauroglycol 90; Capryol 90).

Component (b3) is preferably used in the presence of component (b2) as further component, and is then present in a weight ratio of component (b2) to component (b3) of 0.2 to 10, preferably 4 to 6.5. The combination of component (b2) and (b3) works e.g. as a surfactant/cosurfactant system.

Component (b3), the cosurfactant phase, has a HLB value of about 4 to 10. Propylene glycol monocaprylate like e.g. Capryol 90® (sold by Gattefossé S.A., F-Saint-Priest) and propylene glycol monolaurate, like e.g. Lauroglycol 90® (sold by Gattefossé S.A., F-Saint-Priest) are specifically preferred and very suitable for the present invention.

Component (b3) is preferably used in an amount from about 2.5 to 15 percent by weight of the composition.

Specific compositions according to the present invention comprise a pharmaceutically acceptable acid addition salt of the compound of formula I, like a corresponding hydrochloric acid addition salt and a component (b1), which has a HLB value of about 4 and represents 15 to 20 percent by weight of the composition. Component (b2) of said compositions preferably comprises a caprylocaproyl macrogolglyceride which has a HLB value of about 14 and represents 55 to 65 percent by weight of the composition. More preferably, a component (b3) is also present, which has an HLB value of about 4 to about 7, in particular a propylene glycol monolaurate and has a HLB value of about 5.

Compositions of the aforementioned type include the compositions suitable for oral use which comprises the compound (I-A):

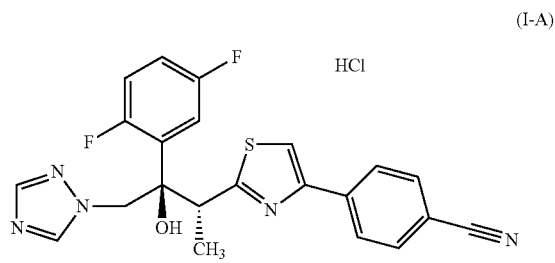 [SMILES: C[C@@H](c1nc(-c2ccc(C#N)cc2)cs1)[C@](O)(Cn1cncn1)c1cc(F)ccc1F ; Cl]

(I-A)

are in the form of a system which is self-microemulsifying on contact with an aqueous phase, and comprises by weight:

5 to 10 percent of the compound (I-A);
15 to 20 percent of Labrafil® M 1944 CS
60 to 65 percent of Labrasol®; and
8 to 12 percent of Lauroglycol® 90.

A specific example of such a composition comprises about:

8 percent of the compound (I-A);
18.4 percent of Labrafil® M 1944 CS
63.1 percent of Labrasol®; and
10.5 percent of Lauroglycol® 90

Preferably the compositions of the present invention, however, comprise the compound of formula I in form of the free base.

Specific embodiments of these preferred compositions comprise component (b1) in an amount of 70 to 95 percent by weight of the composition, and said component (b1) has more preferably a HLB value of about 14.

Yet more preferably, said compositions furthermore comprise a caprylocaproyl macrogolglyceride having a HLB value of about 14 and representing 10 to 20 percent by weight of the composition as component (b2).

Specifically preferred compositions of said type comprise furthermore a component (b3) which has an HLB value of about 4 to about 7, like e.g. a propylene glycol monocaprylate having an HLB value of about 6.

Specific examples of this type of compositions are compositions comprising the compound (I-B):

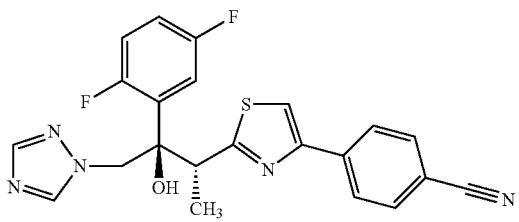

(I-B)

and being in the form of a system which is self-microemulsifying on contact with an aqueous phase, said compositions comprising by weight:
7 to 12 percent of the compound (I-B);
93 to 70 percent of Gelucire® 44/14.

Another embodiment of said compositions comprises (in addition to the aforementioned components (a) and (b1)
(b2) 5 to 20 percent of Labrasol®; and
(b3) 2 to 10 percent of Capryol® 90.

Instead of said components (b2) and (b3), it is also possible to use water-miscible solvents as cosolvents, e.g. polyethylene glycol (e.g. PEG400), ethanol, or diethylene glycol monoethyl ether, e.g. Transcutol®HP, preferably 2 to 10 percent.

Specific pharmaceutical compositions of said type include e.g. the following:

|  | Composition | | |
| --- | --- | --- | --- |
|  | 1 | 2 | 3 |
| (a) | 10% Compound I-B | 10% Compound I-B | 10% Compound I-B |
| (b1) | 90% Gelucire44/14 | 85.5% Gelucire44/14 | 72% Gelucire 44/14 |
| (b2) | — | 4.5% Transcutol | 15.4% Labrasol |
| (b3) | — | — | 2.6% Capryol 90 |
| Sum | 100% | 100% | 100% |

The compositions according to the present invention can e.g. be used in form of fill masses for hard or soft capsules made from gelatin or from vegetable sources like e.g. hypromellose, comprising the composition. Alternatively, the compositions can be applied in the form of oral solutions, either undiluted or diluted with drinking water or other beverages like orange juice.

Another aspect of the invention is the use of the described compositions for the manufacture of a medicament for the oral treatment of systemic mycoses in a mammal, preferably a human, including in particular the treatment of disseminated aspergillosis or candidiasis.

EXAMPLE 1

The following three compositions are prepared

| Comp. | Composition | | |
| --- | --- | --- | --- |
|  | 1.1 | 1.2 | 1.3 |
| (a) | 10% Compound I-B | 10% Compound I-B | 10% Compound I-B |
| (b1) | 90% Gelucire44/14 | 85.5% Gelucire44/14 | 72% Gelucire 44/14 |
| (b2) | — | 4.5% Transcutol | 15.4% Labrasol |
| (b3) | — | — | 2.6% Capryol 90 |
| Sum | 100% | 100% | 100% | using the following method:

A 0.50 g of Compound I-B is placed into a 15 ml screw capped clear glass flask. To this is added 4.50 g of the combination of excipients indicated in the table. The flask is closed and placed in a sonication bath. The temperature of the bath is set at 50° C. for these semi-solid formulations and are sonicated for 90 minutes.

Hard gelatine capsules are filled with 650 mg of the semi-solid formulations and put aside for 24 hours, in order to let the excipients recrystallise entirely. After 24 hours, the instant diluability is evaluated by pouring the contents of one capsule (650 mg of anhydrous formulation) into 900 ml of demineralised water in a standard dissolution vessel at 37° C. equipped with a paddle at a 100 rpm stirring speed. The hard gelatine capsule is removed from the vessel in order to avoid any effect due to the gelatine on the particle size of the solution.

Liquid formulations can be sonicated for 90 minutes at 30° C. and directly evaluated by dropping 650 mg of the formulation into 900 ml of demineralised water in the standard dissolution vessel at 37° C. equipped with paddle at a 100 rpm stirring rate.

Aliquots are taken with a plastic pipette after 30 minutes and the particles' size is measured.

The evaluation of the diluability is done on two criteria, particle size distribution and visual assessment.
1. Particle size distribution is measured using a photon correlation spectrophotometer (PCS). Measurement is done at 37° C. on the sample taken after 30 nm in the dissolution vessel. Particle size is indicated by intensity distribution and shown in the results table as mean peak value. In case of multiple peaks, the population percentage corresponding to each peak has been given (between brackets).
2. Visual assessment of the aspect in the vessel is classified as follows:
  No particle can be seen in suspension and the solution is optically clear
  No particle can be seen in suspension and the solution is turbid
  Particles are observable in suspension or flocculating and the solution is turbid The results are shown in the following table:

| Composition | Particle size after 30 min | Visual aspect at 25° C. |
| --- | --- | --- |
| 1.1 | 200 nm | Slightly opalescent vessel with very fine particles dispersed within the medium that tend to aggregate in time. After 1 hour, white, fluffy flakes sediment at the bottom of the vessel. White turbid medium in the vessels. No sedimentation can be seen at the bottom of the vessel. |
| 1.2 | 249.2 nm | Transparent vessel. After 1 hour, particles in suspension can be seen in the bowl, that sediment once the paddle has stopped. |

-continued

| Composition | Particle size after 30 min | Visual aspect at 25° C. |
|---|---|---|
| 1.3 | 350.3 nm | Slightly turbid after 30 minutes. After 24 hours, a sedimentation can be seen at the bottom of the vessel. |

EXAMPLE 2

The following compositions are prepared as described in Example 1:

| Comp. | Composition 2.1 |
|---|---|
| (a) | 10% Compound I-A |
| (b1) | 18% Labrafil M1944CS |
| (b2) | 61.7% Labrasol |
| (b3) | 10.3% Lauroglycol 90 |
| Sum | 100% |

| Comp. | Composition 2.2 |
|---|---|
| (a) | 10% Compound I-A |
| (b1) | 55.8% Gelucire 44/14 |
| (b1) | 5.4% Gelucire 33/01 |
| | 10.8% Peceol |
| | 14.4% PEG400 |
| | 3.6% Ethanol |
| Sum | 100% |

(Gelucire 33/01: glycerol esters of saturated $C_8$-$C_{18}$ fatty acids, having a HLB value of about 1)

PEG400 and ethanol are co-solvents.

EXAMPLE 3

Four male rats are applied intravenously with 0.5 mg/kg BAL4815 in PEG400/Ethanol/phosphate buffer pH=7.4 (20%/5%/75%) (2 mL/kg). Two male rats/formulation are applied orally in hard gelatine capsule (PcCaps) at a dose of approximately 2 mg/animal. Serial blood samples are collected on heparin from the vena saphena. Blood samples are analyzed using LC-MS/MS method.

Using the linear trapezoidal rules area under the curve (AUC) of the blood concentration time-profiles, the oral bioavailability of the different compositions is calculated as:

$F\% = 100*(AUCpo/(AUCiv)*(Dose\ iv/Dose\ po)$

| Composition | Oral bioavailability F[%] |
|---|---|
| 1.1 | 74% |
| 1.2 | 89% |
| 1.3 | 102% |
| 2.1 | 90% |

All formulations demonstrate the excellent bioavailability of the drug substance in the rat achieved according to the present invention. Trendwise there is an improvement of the oral bioavailability of the drug with composition 1.2, 1.3, and 2.1 over composition 1.1.

The oral bioavailability of composition 2.2 is measured as described above, giving a value of 109%.

EXAMPLE 4

The following composition according to the invention is prepared:

| Comp. | Composition 2.3 [mg/% bw] |
|---|---|
| (a) | 433.3/8 the compound I-A |
| (b1) | 1000.0/18.4 Labrafil ® M 1944 CS |
| (b2) | 3430.0/63.1 Labrasol ® |
| (b3) | 570.0/10.4 Lauroglycol ® 90 |
| Sum | 100% |

The composition represents a colorless to slightly yellowish, viscous solution which is self-emulsifying on contact with aqueous media.

A single dose bioavailability study is conducted on N fasted subjects using the composition of this Example (N=7, dose of compound I-A 433.3 mg corresponding to 400 mg free base of formula I-B), and the same amount in powder form filled into hard capsules, (N=6). BAL8557, a water-soluble prodrug of the compound of formula I-B according to EP-A-1 280 795, is used as a standard (capsule comprising BAL 8557 in powder form in an amount corresponding to 400 mg free base of formula I-B; N=3).

The results of this study are summarized in the following table.

Relative Bioavailability ($F_{rel}$)

| Drug applied | Galenical formulation | $T_{1/2}$ [h] | $T_{max}$ [h] | $C_{max}$ [ng·h/ml] | $AUC_{infinite}$ [ng·h/ml] | $F_{rel}$* [%] |
|---|---|---|---|---|---|---|
| I-A | Example 4 | 88 | 1.5 | 4413 | 192719 | 90 |
| I-A | Powder in capsule | 108 | 3 | 859 | 62772 | 30 |
| BAL 8557 | Powder in capsule | 56 | 3 | 5566 | 215413 | 100 |

From these data it is seen that formulating compound I-A according to the present invention significantly increases the speed of resorption (cf. $T_{max}$) as well as the bioavailability, which is increased by a factor of 3 in case of the present formulation and thus comparable to that of a water-soluble prodrug of said compound like BAL 8557.

What is claimed is:

1. A pharmaceutical composition for oral administration which is self-emulsifying on contact with an aqueous phase which comprises:

(a) an antifungally active compound of formula (I):

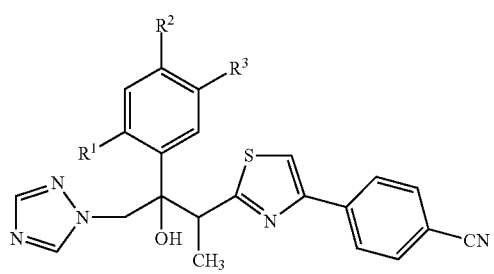

wherein
R[1], R[2] and R[3] are independently of one another hydrogen, F or Cl; or
a pharmaceutically acceptable acid addition salt thereof; and
a carrier which self-emulsifies said antifungal compound on contact with the aqueous phase, wherein the carrier comprises:
(b) a solubilizer component for the antifungally effective component (a) and having an HLB value of less than 20, said solubilizer component comprising:
(b1) a mixture of glycerol mono-, di- and/or triesters and of polyethylene glycol mono- and/or diesters, said esters being formed with at least one fatty acid selected from the group consisting of lauric acid and oleic acid; and/or
(b2) a mixture of glycerol mono-, di- and/or triesters and of polyethylene glycol mono- and/or diesters, said esters being formed with caprylic acid and capric acid,
wherein the antifungally active compound of formula (I) or the pharmaceutically acceptable acid addition salt thereof is present in an amount of about 5 to 15 percent by weight based on the weight of the total composition, and wherein
component (b1) is present in an amount of 50 or more than 50 percent by weight based on the total weight of the composition and in an amount of 70 or more than 70 percent by weight of the total weight of the carrier, when said pharmaceutical composition comprises the antifungally active compound of formula (I) in form of the free base, or
component (b2) is present in an amount of 50 or more than 50 percent by weight based on the total weight of the composition and in an amount of 65 or more than 65 percent by weight of the total weight of the carrier, when said pharmaceutical composition comprises a pharmaceutically acceptable acid addition salt of a compound of formula (I).

2. The composition of claim 1, wherein
R[1] is F or Cl; and
R[2] and R[3] are independently of one another hydrogen, F or Cl.

3. The composition of claim 2, wherein
R[1] and R[2] are F; and
and R[3] is hydrogen.

4. The composition of claim 2, wherein
R[1] and R[3] are F; and
and R[2] is hydrogen.

5. The composition of claim 1 comprising a mixture of a component (b1) and a component (b2).

6. The composition of claim 5, comprising an antifungally active compound of formula (I) in form of the free base.

7. The composition of claim 1, comprising a pharmaceutically acceptable acid addition salt of a compound of formula (I).

8. The composition of claim 1, comprising a solubilizer component (b), wherein the carrier comprises:
(b3) a further component comprising at least one ester of an alcohol, said esters being formed from at least one fatty acid selected from the group consisting of caprylic esters of propylene glycol, lauric esters of propylene glycol and oleic esters of polyglycerol.

9. The composition of claim 5, wherein the carrier comprises:
(b3) a further component comprising at least one ester of an alcohol with at least one fatty acid selected from group comprising caprylic esters of propylene glycol, lauric esters of propylene glycol and oleic esters of polyglycerol and
the weight ratio of component (b2) to component (b3) is from about 0.2 to 10.

10. The composition of claim 5, wherein component (b1) has a HLB value of about 4 and is present in an amount of from about 15 to 20 percent by weight of the composition.

11. The composition of claim 5, wherein component (b1) has a HLB value of about 4 and is present in an amount of from about 15 to 20 percent by weight of the composition and component (b2) comprises a caprylocaproyl macrogolglyceride, has a HLB value of about 14 and is present in an amount of from about 55 to 65 percent by weight of the weight of the composition.

12. The composition of claim 11, wherein the carrier comprises:
(b3) a further component comprising at least one ester of an alcohol with at least one fatty acid selected from group comprising caprylic esters of propylene glycol, lauric esters of propylene glycol and oleic esters of polyglycerol and
said component (b3) has an HLB value of from about 4 to about 7.

13. The composition of claim 12 wherein component (b3) comprises a propylene glycol monolaurate and has a HLB value of about 5.

14. A composition for preparing a dosage form for oral use which comprises the compound (I-A):

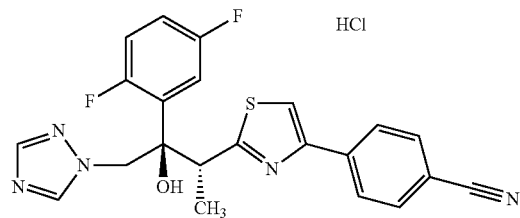

(I-A)

in the form of a system which is self-(micro)emulsifying on contact with an aqueous phase, and comprises by weight:
from about 5 to 10 percent of the compound (I-A);
from about 15 to 20 percent of Labrafil® M 1944 CS
from about 60 to 65 percent of Labrasol®; and
from about 8% to 12 percent of Lauroglycol® 90.

15. The composition of claim 14, which comprises about:
8 percent of the compound (I-A);
18.4 percent of Labrafil® M 1944 CS
63.1 percent of Labrasol®; and
10.6 percent of Lauroglycol® 90.

16. The composition of claim 6, wherein component (b1) has a HLB value of about 14 and is present in an amount of from about 70 to 95 percent by weight of the composition.

17. The composition of claim 16, wherein component (b2) comprises a caprylocaproyl macrogolglyceride, has a HLB value of about 14 and is present in an amount of from about 10 to 20 percent by weight of the composition.

18. A composition for preparing a dosage form for oral use which comprises the compound (I-B):

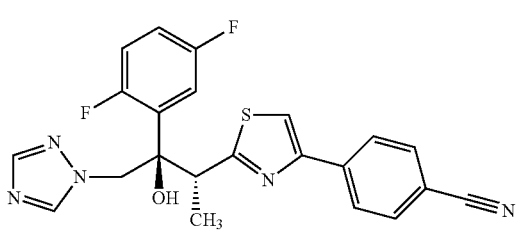

(I-B)

in the form of a system which is self-microemulsifying on contact with an aqueous phase, and comprises by weight based upon the weight of the composition:
from about 7 to 12 percent of the compound (I-B); and
from about 70 to 93 percent of Gelucire® 44/14.

19. The composition of claim 18, further comprising from about 5 to 20 percent by weight of Labrasol®; and from about 2 to 10 percent by weight of Capryol® 90, based upon the weight of the composition.

20. The composition of claim 18, further comprising a water-miscible solvent or a mixture thereof as cosolvent.

21. The composition of claim 18 selected from the compositions of the following table:

| Comp. | Composition | | |
|---|---|---|---|
| | 1.1 | 1.2 | 1.3 |
| (a) | 10% Compound I-B | 10% Compound I-B | 10% Compound I-B |
| (b1) | 90% Gelucire44/14 | 85.5% Gelucire44/14 | 72% Gelucire 44/14 |
| (b2) | — | 4.5% Transcutol | 15.4% Labrasol |
| (b3) | — | — | 2.6% Capryol 90 |
| Sum | 100% | 100% | 100%. |

22. The pharmaceutical composition of claim 1 wherein said aqueous phase is a gastrointestinal fluid.

23. The composition of claim 1 wherein said compound or its salt is present in an amount of from about 7% to about 12% by weight based upon the total weight of the composition.

24. The composition of claim 7 wherein said salt is a hydrochloric acid addition salt.

25. The composition of claim 9 wherein the weight ratio of component (b2) to component (b3) is from about 4 to about 6.5.

26. The composition of claim 5 wherein the carrier comprises:
(b3) a further component comprising at least one ester of an alcohol with at least one fatty acid selected from group comprising caprylic esters of propylene glycol, lauric esters of propylene glycol and oleic esters of polyglycerol and
component (b1) has a HLB value of about 14 and is present in an amount of from about 70 to about 95 percent by weight of the composition.

27. The composition of claim 5 wherein the carrier comprises:
(b3) a further component comprising at least one ester of an alcohol with at least one fatty acid selected from group comprising caprylic esters of propylene glycol, lauric esters of propylene glycol and oleic esters of polyglycerol;
component (b1) has a HLB value of about 14 and is present in an amount of from about 70 to 95 percent by weight of the composition and
component (b2) comprises a caprylocaproyl macrogolglyceride, has a HLB value of about 14 and is present in an amount of from about 10 to about 20 percent by weight of the composition.

28. The composition of claim 27 wherein the component (b3) has an HLB value of from about 4 to about 7.

29. The composition of claim 28 wherein component (b3) comprises a propylene glycol monocaprylate and has a HLB value of about 6.

30. The composition of claim 20 wherein the cosolvent is diethylene glycol monoethyl ether.

31. A composition according to claim 5, wherein the carrier comprises:
(b3) a further component comprising at least one ester of an alcohol with at least one fatty acid selected from group comprising caprylic esters of propylene glycol, lauric esters of propylene glycol and oleic esters of polyglycerol and
component (b2) comprises a caprylocaproyl macrogolglyceride, has a HLB value of about 14 and represents 10 to 20 percent by weight of the composition.

32. A composition according to claim 31, wherein the component (b3) has an HLB value of about 4 to about 7.

33. A pharmaceutical composition for oral administration which is self-emulsifying on contact with an aqueous phase which comprises:
(a) 10% Compound 1-A
(b1) 55.8% Gelucire 44/14
(b1) 5.4% Gelucire 33/01
10.8% Peceol
14.4% PEG400
3.6% Ethanol.

* * * * *

UNITED STATES PATENT AND TRADEMARK OFFICE
CERTIFICATE OF CORRECTION

PATENT NO. : 8,536,208 B2
APPLICATION NO. : 12/674048
DATED : September 17, 2013
INVENTOR(S) : Bucher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 765 days.

Signed and Sealed this
Fifteenth Day of September, 2015

Michelle K. Lee
*Director of the United States Patent and Trademark Office*